(12) United States Patent
Bae et al.

(10) Patent No.: US 9,569,590 B2
(45) Date of Patent: Feb. 14, 2017

(54) APPARATUS FOR MEASURING BIOLOGICAL INFORMATION AND METHOD FOR COMMUNICATING DATA FROM APPARATUS FOR MEASURING BIOLOGICAL INFORMATION

(71) Applicant: INFOPIA CO., LTD., Anyang-si, Gyeonggi-do (KR)

(72) Inventors: Byeong Woo Bae, Anyang-si (KR); Sung Dong Lee, Anyang-si (KR); Hong Seong Suk, Anyang-si (KR); Kyu Won Lee, Anyang-si (KR)

(73) Assignee: INFOPIA CO., LTD., Anyang-si (KR)

( * ) Notice: Subject to any disclaimer, the term of this patent is extended or adjusted under 35 U.S.C. 154(b) by 13 days.

(21) Appl. No.: 14/398,610

(22) PCT Filed: May 2, 2013

(86) PCT No.: PCT/KR2013/003816
§ 371 (c)(1),
(2) Date: Nov. 3, 2014

(87) PCT Pub. No.: WO2013/165195
PCT Pub. Date: Nov. 7, 2013

(65) Prior Publication Data
US 2015/0110092 A1 Apr. 23, 2015

(30) Foreign Application Priority Data
May 4, 2012 (KR) .................. 10-2012-0047675

(51) Int. Cl.
*G06F 19/00* (2011.01)
*H04W 4/00* (2009.01)
(Continued)

(52) U.S. Cl.
CPC ............ *G06F 19/324* (2013.01); *A61B 5/0022* (2013.01); *G06F 19/3418* (2013.01);
(Continued)

(58) Field of Classification Search
None
See application file for complete search history.

(56) References Cited

U.S. PATENT DOCUMENTS 9,241,237 B2 * 1/2016 Hirsch .................... H04L 63/18
2004/0100376 A1 * 5/2004 Lye ........................ A61B 5/411
340/539.12
(Continued)

FOREIGN PATENT DOCUMENTS

JP 2002-330142 A 11/2002
JP 2010-278851 A 12/2010
(Continued)

OTHER PUBLICATIONS

International Search Report dated Jun. 21, 2013, issued in corresponding application No. PCT/KR2013/003816.
(Continued)

*Primary Examiner* — Robert C Scheibel
(74) *Attorney, Agent, or Firm* — Westerman, Hattori, Daniels & Adrian, LLP (57) ABSTRACT

The present invention relates to an apparatus for measuring biological information supporting multiplex communication. The apparatus for measuring biological information, according to one embodiment of the present invention, comprises: a measuring portion for measuring biological information through a biosensor; a data communication portion for transreceiving the biological information that is measured with an external device through a wireless communication network, which supports a client mode and an AP mode; and a control portion for accessing a communi-
(Continued)

cation network by controlling the client mode or the AP mode in a WiFi module. The present invention can transmit data to the external device through a connected AP by operating a wireless communication module in the client mode, or communicate data with the external device through a communication module of terminals, which connect by self-switching to the AP mode when the connected AP does not exist.

13 Claims, 5 Drawing Sheets

(51) Int. Cl.
    *A61B 5/00*     (2006.01)
    *A61B 5/0205*     (2006.01)
    *H04W 84/12*     (2009.01)
    *H04W 92/10*     (2009.01)

(52) U.S. Cl.
    CPC ........... H04W 4/005 (2013.01); H04W 4/008 (2013.01); *A61B 5/002* (2013.01); *A61B 5/0205* (2013.01); *H04W 84/12* (2013.01); *H04W 92/10* (2013.01)

(56) References Cited

U.S. PATENT DOCUMENTS

| | | | | |
|---|---|---|---|---|
| 2005/0261564 | A1* | 11/2005 | Ryu | A61B 5/6804 600/388 |
| 2006/0077997 | A1* | 4/2006 | Yamaguchi | H04L 12/2803 370/445 |
| 2010/0046468 | A1* | 2/2010 | Oi | H04W 84/20 370/331 |
| 2010/0303001 | A1* | 12/2010 | Tamura | H04W 88/06 370/315 |
| 2012/0019386 | A1* | 1/2012 | Doraiswami | G01N 33/48792 340/573.1 |
| 2012/0099572 | A1* | 4/2012 | Kato | H04W 88/06 370/338 |
| 2012/0156933 | A1* | 6/2012 | Kreger | A61B 5/02433 439/625 |
| 2013/0116584 | A1* | 5/2013 | Kapoor | A61B 5/02 600/513 |
| 2013/0211265 | A1* | 8/2013 | Bedingham | G06F 19/3418 600/483 |

FOREIGN PATENT DOCUMENTS

| | | |
|---|---|---|
| KR | 10-2005-0111082 A | 11/2005 |
| KR | 10-0979274 B1 | 8/2010 |
| KR | 10-1114164 B1 | 2/2012 |
| WO | 2009-107040 A1 | 9/2009 |

OTHER PUBLICATIONS

Extended (Supplementary) Search Report dated Apr. 18, 2016, issued in European Application No. 13784970.9 (10 pages).
Higgins, Tim, "How to Convert a Wireless Router into an Access Point", SmallNetBuilder, Mar. 10, 2008, URL: http://www.smallnetbuilder.com/basics/wireless-basics/30338-how-to-convert-a-wireless-router-into-an-access-point?tmpl=component&print=1&layout=default&page= (4 pages).
Anonymous, "Wi-Fi Direct", Wikipedia, the free encyclopedia, Apr. 28, 2012, "https://en.wikipedia.org/w/index.php?title=Wi-Fi_Direct&oldid=489595043" (4 pages).

* cited by examiner

APPARATUS FOR MEASURING BIOLOGICAL INFORMATION AND METHOD FOR COMMUNICATING DATA FROM APPARATUS FOR MEASURING BIOLOGICAL INFORMATION

TECHNICAL FIELD

The following description relates to an apparatus for measuring biological information and a technology of transmitting data measured by the apparatus to an external device.

BACKGROUND ART

In general, diagnostic devices that measure biological information of a user employs various communication methods to transmit measurement data to an external device, such as a computer and a mobile device. For example, a diagnostic device may connect to an external device using a cable or a USB for transmission. Recently, a technology has been developed of transmitting data using mobile devices, such as a gateway, a mobile phone, and a tablet, in which a short-range wireless communication module, such as a Bluetooth module and a Zigbee module, is equipped.

Korean Patent No. 10-0979274 introduced a technique of transmitting biological information through a USB or Bluetooth communication interface. However, when transmitting measurement results to a server over a network connection, most of the biological information measuring devices need to associate with a specific gateway, so that it is impossible to transmit data adaptively according to various communication environments.

Technical Problem

The following description relates to an apparatus and method, which allows uploading of data to an external device through a connected terminal by setting a wireless communication module in an AP mode in a case where there is no accessible AP in surroundings of an apparatus for measuring biological information.

The following description relates to an apparatus and method, which allow active access to a communication network according to various communication environments and transmission of biological information to an external device using a biological information measuring device equipped with a short-range wireless communication module or a mobile communication module.

Technical Solution

In one general aspect, there is provided an apparatus for measuring biological information, including: a measuring portion configured to measure biological information using a biosensor; a data communication portion configured to comprise a wireless communication module comprising a WiFi module that supports a client mode and an Access Point (AP) mode, and to transceive the measured biological information with an external device over an accessed communication network; and a control portion configured to control the client mode or the AP mode of the WiFi module to access a communication network.

The control portion may be further configured to comprise an AP search portion configured to search any adjacent accessible AP; and a mode setting portion configured to set the WiFi module in the client mode in a case where an AP is found by the AP search portion, and set the WiFi module in the AP mode in a case where no AP is found by the AP search portion.

The data communication portion may transmit data to the external device through the found AP in response to the WiFi module set in the client mode, and transmits data to the external device by way of a terminal accessing the apparatus in response to the WiFi module set in the AP mode.

The control portion may be further configured to comprise a terminal control portion configured to, in response to the WiFi module set in the AP mode, control a communication module included in any one terminal accessing the apparatus so as to control access to the communication network through the communication module.

The measuring portion may be further configured to comprise a sensor connector configured to connect a biosensor; and a signal processor configured to convert biological signal measured by the biosensor into biological information, wherein the apparatus further comprises a storage configured to store the converted biological information; and a display configured to display the converted biological information.

The wireless communication module may further comprise one or more of a Bluetooth module, a Zigbee module, an ANT module, and a Near Field Communication (NFC) module.

The data communication portion may be further configured to receive, from an NFC terminal connected through the NFC module, connection information of a wireless communication module equipped in the NFC terminal, wherein the apparatus further comprises a setting portion configured to set connection information of a corresponding wireless communication module by using the received connection information.

The data communication portion may be further configured to comprise a mobile communication module that comprises a third-generation (3G) or fourth-generation (4G) mobile communication module, wherein the control portion controls any one communication module based on a communication network access status of a wireless communication module and a mobile communication module, or based on information on a user preferred network so as to access a communication network.

In another general aspect, there is provided a method for communicating data in an apparatus for measuring biological information, the method including controlling, by the apparatus, access to a communication network through a client mode and an Access Point (AP) mode of a WiFi module; and transceiving data including biological information with respect to an external device over the communication network.

The controlling of access to a communication network may include searching for an adjacent accessible AP; and setting a WiFi module in a client mode when the adjacent accessible AP is found by the AP search portion, and setting the WiFi module in an AP mode in a case where the adjacent accessible AP is not found by the AP search portion.

The transceiving of data may comprise, in response to the WiFi module set in the client mode, transmitting the data to an external device through the found AP, and, in response to the WiFi module set in the AP mode, transmitting the data to the external device by way of a terminal accessing the apparatus.

The controlling of access to a communication network may comprise, in response to the WiFi module set in the AP mode, controlling the access to the communication network by controlling a communication module included in any one terminal assessing the apparatus.

The wireless communication module may comprise one or more of a Bluetooth module, a Zigbee module, an ANT module, and a Near Field Communication (NFC) module.

The method may further include, prior to the controlling of access to the communication network, receiving connection information of a wireless communication module equipped in an NFC terminal connected through the NFC module; and setting connection information of a corresponding wireless communication module by using the received connection information.

Advantageous Effects

It is possible to transmit data to an external device through a connected AP by selectively setting a wireless communication module in a client mode or, if there is no connected AP, by self-shift to an AP mode to perform data communication with an external device through communication modules of connected terminals.

In addition, by receiving connection setting information of various communication modules from NFC devices connected over NFC communication that does not require additional settings, and by automatically setting a communication module of an apparatus for measuring biological information, it is possible to enhance convenience of a user interface.

Having a wireless communication module, such as a WiFi module, or a third-generation (3G)/four-generation (4G) mobile communication module being equipped therein, an apparatus for measuring biological information may actively access a communication network according to various communication environments, regardless of whether a system is a gateway system or a backend system, and transmit biological information to an external device.

DESCRIPTION OF DRAWINGS

The accompanying drawings, which are included to provide a further understanding of the invention and are incorporated in and constitute a part of this specification, illustrate embodiments of the invention, and together with the description serve to explain the principles of the invention.

MODE FOR INVENTION

The invention is described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements. Hereinafter, an apparatus for measuring biological information and a method for communicating data in the apparatus are described in detail with reference to drawings.

Figure 1:
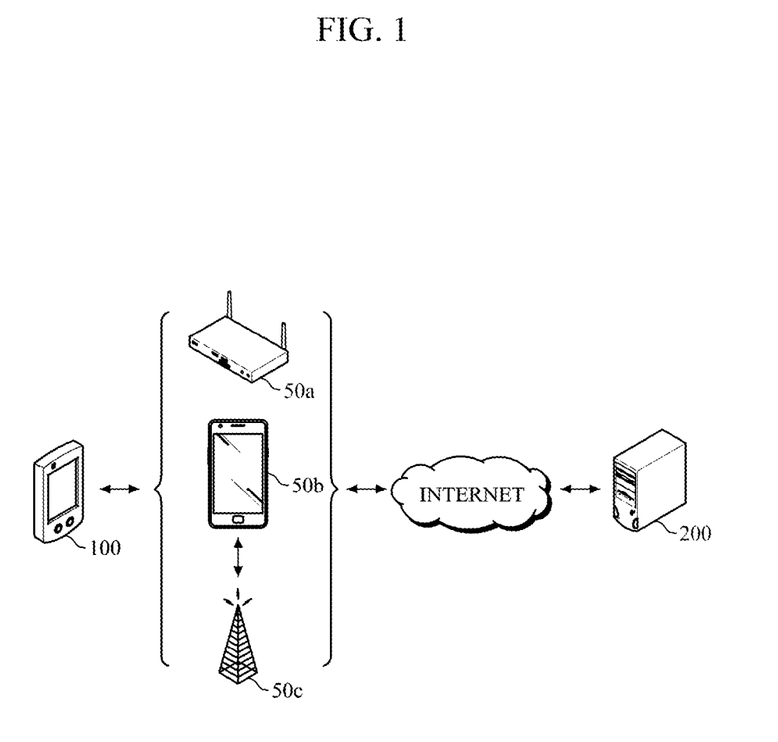
FIG. 1 is a diagram illustrating a case where an apparatus for measuring biological information communicates data with an external device according to an exemplary embodiment.

FIG. 1 is a diagram illustrating a case where an apparatus 100 for measuring biological information performs data communication with an external device 200 according to an exemplary embodiment.

Referring to FIG. 1, the apparatus 100 may transmit measured biological information and various kinds of data to the external device 200, or receive various kinds of data from the external device 200. The external device 200 may include any different kind of diagnostic devices, a mobile device, for example, a smart phone, and a tablet PC, a laptop, a desktop PC, a server, and a cloud. The apparatus 100 may include various communication modules, and may perform data communication with the external device 100 in various ways by controlling various communication modules to be adequate for a communication environment.

According to an embodiment, the apparatus may access the Internet through an adjacent Access Point 50a and then perform data communication with the external device 200. At this point, the AP 50a may be a mobile terminal that supports a Hot-Spot function, and, in this case, the apparatus 100 accesses the mobile terminal using WiFi, and the mobile terminal connects the external device 200 by connecting the communication network using a mobile communication module.

According to another embodiment, in a case where there is no adjacent accessible AP 50a, the apparatus 100 may act as an AP and wait for access of an adjacent mobile terminal 50b, and, in response to the access of the mobile terminal 50b, perform data communication with the external device 200 by bypassing the mobile terminal 50b. That is, the apparatus 100 performs data communication with the external device 200 using a wireless communication module or a mobile communication module of the mobile terminal 50b. At this point, the apparatus 100 may transmit data including biological information to the mobile terminal 50b, and transmit the same data to the external device 200 by manipulating an interface of the mobile terminal 50b. Alternatively, the apparatus 100 may perform data communication with the external device 200 by directly controlling a communication module of the accessed mobile terminal 50b.

According to yet another embodiment, the apparatus 100 may include a mobile communication module equipped therein, the mobile communication module, which supports either the third-generation communication, i.e., Global System for Mobile communications (GSM) and wideband code division multiple access (WCDMA), or the fourth generation communication, i.e., wibro, Wi-Max, Long Term Evolution (LTE) and LTE advanced, and the apparatus 100 may perform data communication by controlling the mobile communication module to access the external device 200 through a base station 50c.

Figure 2:
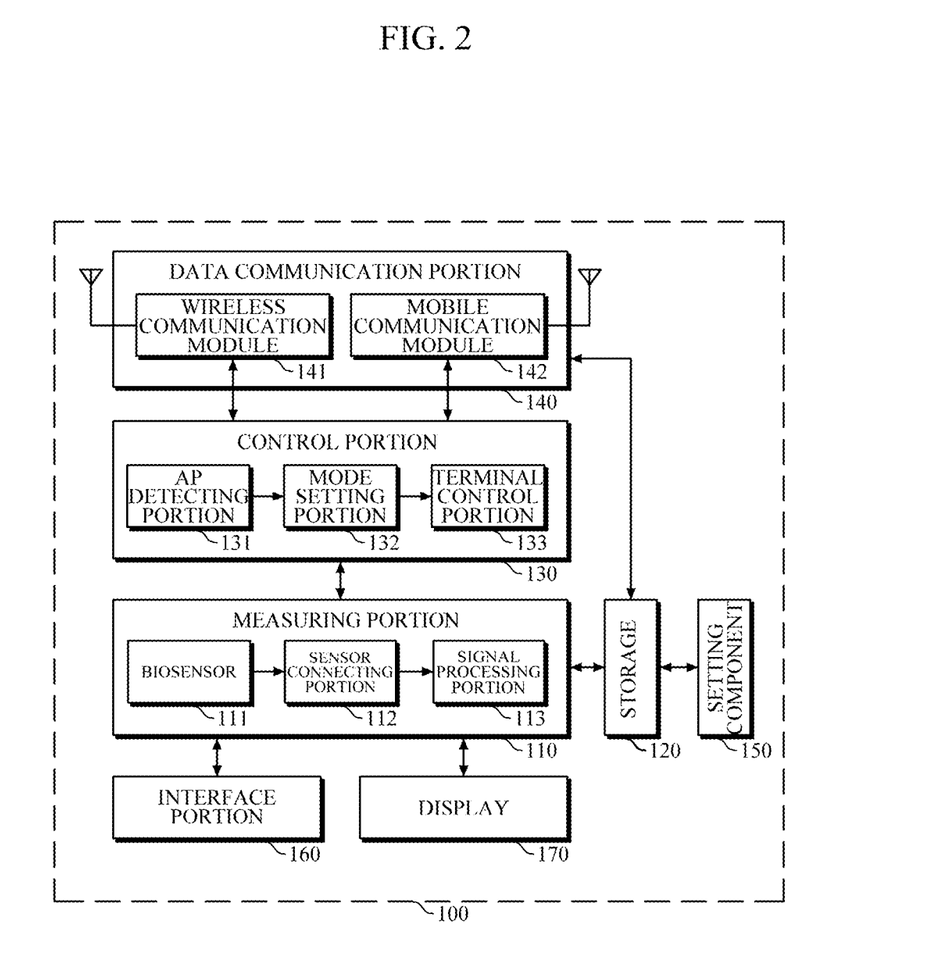
FIG. 2 is a block diagram illustrating the apparatus according to an exemplary embodiment.

FIG. 2 is a block diagram illustrating an apparatus for measuring biological information according to an exemplary embodiment. Referring to FIG. 2, an apparatus 100 for measuring biological information includes a measuring portion 110, a storage 120, a control portion 130, and a data communication portion 140.

The measuring portion 110 may measure biological information and store the biological information in the storage 120. Specifically, the measuring portion 110 may include a bio sensor 111, a sensor connector 112, and a signal processor 113, and may measure a biological signal using the bio sensor 111. The bio sensor 111 may measure various biological signals, such as blood sugar level, blood pressure level, hyperlipidemia, human body fat, electrocardiography, and momentum.

The signal processor 113 may convert the biological signal measured by the bio sensor 111 into numeric biological information.

The storage 120 may store biological information measured by the measuring portion 110 and various kinds of setting information. The various kinds of setting information may include general setting information of functions of the apparatus 100, setting information of an equipped communication module, and criterion information for measurement of a user's biological information. In addition, the storage 120 may further store personal information of a user. At this point, the personal information may include name, gender, age weight, and height of the user.

The control portion 130 may access a communication network by controlling various communication modules equipped in the apparatus 100 and connect the external device 200 over a communication network accessed by the data communication portion 140, so that data communication may be enabled.

The data communication portion 140 may further include a wireless communication module 141 including a WiFi module, and may transceive biological information and various kinds of data by connecting the external device 200 over a communication network accessed by the control portion 130. Further, the wireless communication module 141 may further include one or more of a Bluetooth module, a Zigbee module, an ANT module, and a Near Field Communication (NFC) module.

According to this exemplary embodiment, a WiFi module may support a client mode, which allows access to a communication network using the adjacent AP 50a, and an AP mode in which the apparatus 100 acts as an AP.

In a case where there is a terminal that supports Bluetooth, Zigbee or NFC communication, the control portion 130 may control a corresponding communication module to connect the terminal. In addition, the control portion 130 may control a client mode or an AP mode of the WiFi module to access the communication network.

Specifically, how the control portion 130 accesses a communication network by controlling a WiFi module is described in detail. The control portion 130 may include an AP detector 131 and a mode setting portion 132. The AP detector 131 may search for an adjacent accessible AP 50a. The mode setting portion 132 may set a WiFi module in a client mode in a case where the AP detector 131 detects the AP 50a, and may set the WiFi module in an AP mode to cause the apparatus 100 to act as an AP in a case where the apparatus 100 fails to detect the AP 50a.

In the client mode, the data communication portion 140 may transceive data with respect to the external device 200 by connecting to the external device 200 over an accessed communication network. In a case where the WiFi module is set in the AP mode, the data communication portion 140 may wait for access of the mobile terminal 50b and transmit data to the external device 200 by way of the mobile terminal 50b that is accessing an AP of the apparatus 100.

According to one aspect, the data communication portion 140 may transmit data to the mobile terminal 50b and transmit the data to the external device 200 by manipulating an interface of the mobile terminal 50b.

According to another aspect, under the control of the control portion 130, the data communication portion 140 may transmit data to the external device 200 over a communication network accessed through a communication module of the accessed mobile terminal 50b. That is, the control portion 130 may further include a terminal control portion 133, and, in response to access by the mobile terminal 50b to the apparatus 100, the terminal control portion 133 may directly control a communication module of the mobile terminal 50b to access a communication network. For example, the control portion 130 may control a communication module of the mobile terminal 50b to access the communication network.

According to another embodiment, the data communication portion 140 may receive, from an NFC terminal connected using an NFC module, connection information of a WiFi module equipped in the NFC terminal, such as AP access information of a WiFi module (ID, password, MAC address, and the like), and Bluetooth pairing information. NFC communication does not require additional pairing setting, so that it is possible to easily acquire necessary information from terminals having an NFC communication module equipped therein or an NFC tag attached thereto. In addition, the received connection information may be stored in the storage 120.

At this point, the biological information measuring apparatus 100 may further include a setting portion 150. The setting portion 150 may set connection information of a corresponding communication module using the connection information received by the data communication portion 140.

The apparatus 100 may include an interface portion 160 that provides interface to receive various kinds of information from a user and processes the received information in response to manipulation of the interface by the user. The user may input, to the interface (i.e., various buttons and the like), a request for measurement of a biological signal, a request for display of biological information, a request for communication with the external device 200, and user information. However, the primary function of the apparatus 100 is measuring biological information, so a user may feel inconvenient when inputting a large amount of information, such as access information of the AP 50a and user information, which are required for communication with the external device 200.

According to this embodiment, a user receives various kinds of access information from an accessible NFC terminal without a special setting procedure and automatically sets the received access information, so that the user does not need to input a large amount of information on his own, thereby making a user interface greatly convenient.

According to another aspect, the data communication portion 140 may further include a mobile communication module 142 that supports third-generation (3G) or fourth-generation (4G) communication.

The control portion 130 may access a communication network by way of a base station 50c, by controlling the mobile communication module, if possible. For example, the control portion 130 may to access a communication network using an adjacent accessible AP 50a, by controlling the wireless communication module 141. If there is no adjacent accessible AP 50a, the control portions 130 may access the communication network by controlling the mobile communication module 142. In a case where there is an accessible AP 50a but a communication status is not stable, the control portion 130 may control the mobile communication module 142 to access a mobile communication network.

The control portion 130 may control either or both of the wire communication module 141 or a mobile communication module 142 based on information of a user's preferred network. For example, a user may prefer a wireless communication network that does not require additional costs. In another example, if a user has no extra burden of paying costs, the user may prefer a mobile communication network that supports stable access. The control portion 130 may control the wireless communication module 141 or a mobile communication module 142 based on the preferred network information.

According to another aspect, the data communication portion 140 may further include a memory card module (now shown) and a card slot (not shown). The data communication portion 140 may perform data communication with various mobile memory cards included in the card slot (not shown) through the memory card module (not shown). The mobile memory card may include USB, Compact Flash Memory, Compact Flash Card, a smart media, memory stick, and SD memory card; however, aspects of the present disclosure are not limited thereto, and the mobile memory card may include various mobile memory cards that are expected to be developed due to the advancement of the technologies.

According to additional aspect, the apparatus 100 may further include a display 170.

The display 170 may display measured biological information and various kinds of information. When the measuring portion 110 measures biological information, the display 170 may display the measured biological information. In addition, if the measured biological information exceeds a preset reference level that is retrieved from the storage 120, the display 170 may set off an alarm bell or turn on a display lamp.

For example, if the reference levels are set as three stages, such as stable, dangerous, and very dangerous, an alarm bell corresponding to a stage of measured biological information may be set off. That is, if measured biological information is within the 'stable' stage, an alarm bell is set off once (beep), and, if measured biological information is within the 'dangerous' stage, an alarm bell is set off twice (beep beep). If measured biological information is within the 'very dangerous' stage, an alarm bell may be set off constantly while a display lamp may be on continuously.

The apparatus 100 may further include a statistics portion (now shown). The statistics portion (not shown) may generate not just history of measured biological information, but various kinds of statistical information. The generated statistical information may be transmitted to the external device 200 through the data communication portion 140.

Figure 3:
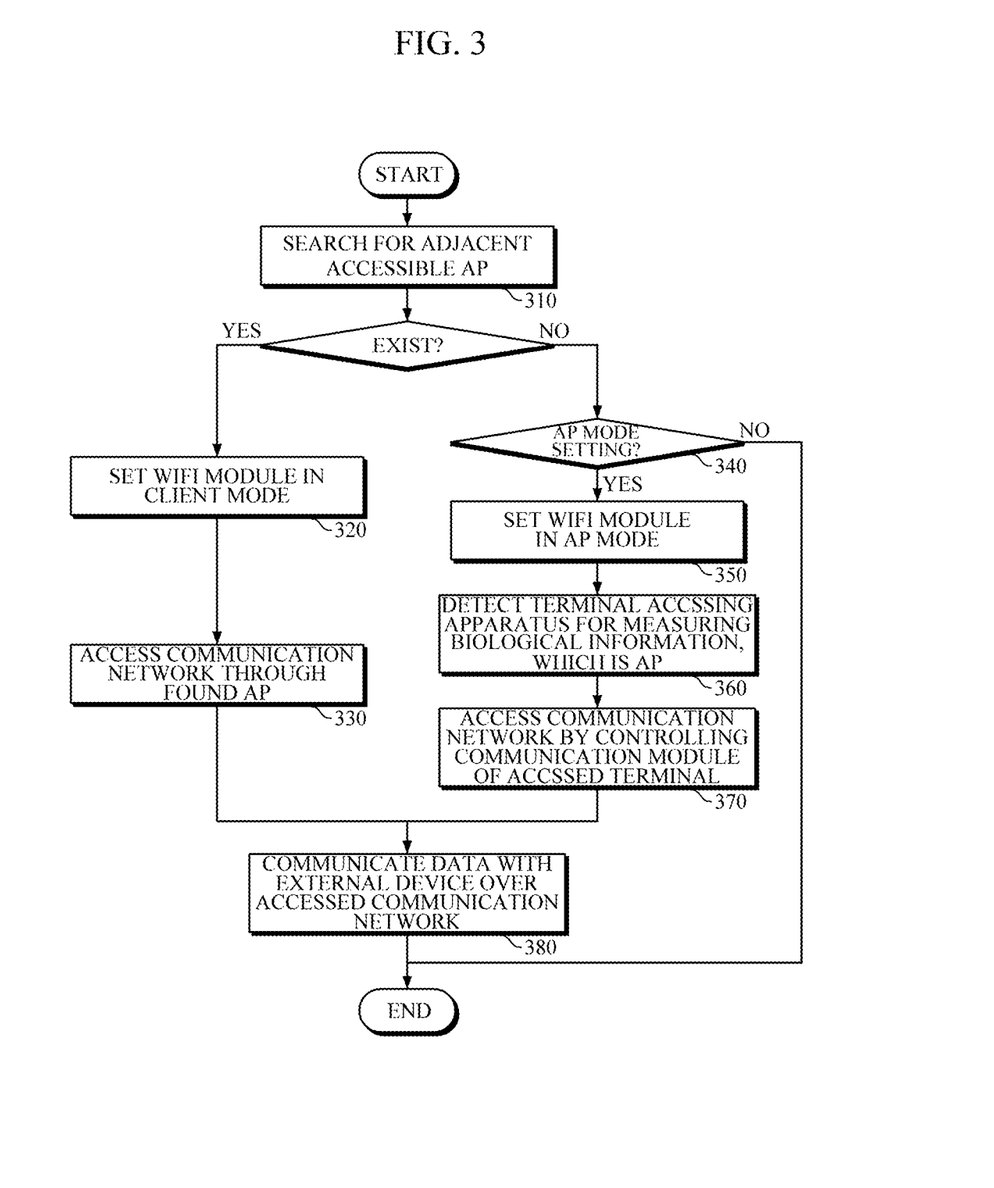
FIG. 3 is a data communication procedure in the apparatus according to an exemplary embodiment.

FIG. 3 is a data communication procedure in the apparatus 100 according to an exemplary embodiment. Referring to FIG. 3, an example in which the apparatus 100 performs data communication with the external device 200 is described.

Firstly, the apparatus 310 searches for an adjacent accessible AP 50a in 310, and, if the AP 50a is found, sets a WiFi module in a client mode in 320. Then, the apparatus 100 accesses a communication network through the found AP 50a in 330, and performs data communication by connecting to the external device 200 over the accessed communication network in 380.

If no adjacent accessible AP 50a is found, the apparatus 100 may check whether to act as an AP in 340; that is, checking whether to set the WiFi module in an AP mode. A user may set in advance whether to automatically set the WiFi module in an AP mode in a case where no adjacent AP 50a is found. Alternatively, the user may input request information by manipulating an interface to set the WiFi module to an AP mode.

In 350, the WiFi module may be set to AP mode in a case where no adjacent AP 50a is found or where a user's request information is input.

Then, the apparatus 100 may detect a mobile terminal 50b, which is accessing the apparatus 100 through the set AP, in 360, and access a communication network by controlling a communication module of the mobile terminal 50b in 370.

Then, the apparatus 100 may perform data communication with the external device 200 over the communication network in 380.

Figure 4:
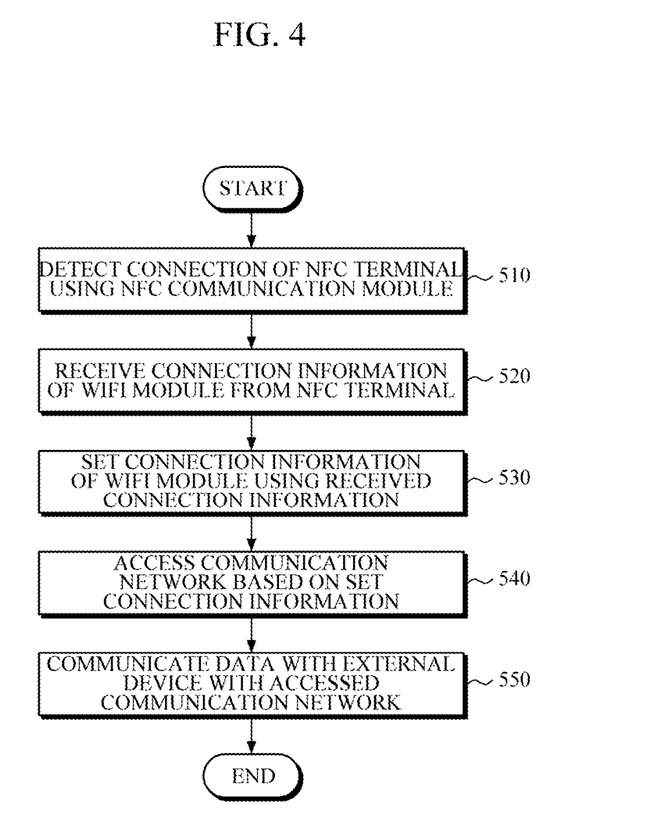
FIG. 4 is a data communication procedure in the apparatus according to another exemplary embodiment.

FIG. 4 is a data communication procedure in the apparatus 100 according to another exemplary embodiment. Referring to FIG. 4, another example of a data communication procedure in the apparatus 100 is described.

Firstly, the apparatus 100 may detect connection of an NFC terminal through an NFC communication module in 510. The NFC terminal may be a terminal having an NFC communication module equipped therein or an NFC tag attached thereto. In addition, the NFC terminal may be a device having a wireless communication module, such as a WiFi module and a Bluetooth module, which is equipped therein, and communication network connection information of the WiFi module or the Bluetooth module (e.g., the WiFi module's AP access ID, password, MAC address, and Bluetooth pairing information) may be set in the NFC terminal.

Then, the apparatus 100 may receive connection information of the mobile communication module from the connected NFC terminal in 520.

In 530, it is possible to set connection information of a corresponding mobile communication module equipped in the apparatus 100 by using the received connection information.

The apparatus 100 may access a communication network based on the set connection information in 540, and perform data communication with the external device 200 over the accessed communication network in 550.

According to this embodiment, by receiving various kinds of connection information from an accessible NFC terminal without a special setting procedure and automatically setting the received information, a user does not need to input a large amount of information, thereby enhancing convenience of a user interface greatly.

Figure 5:
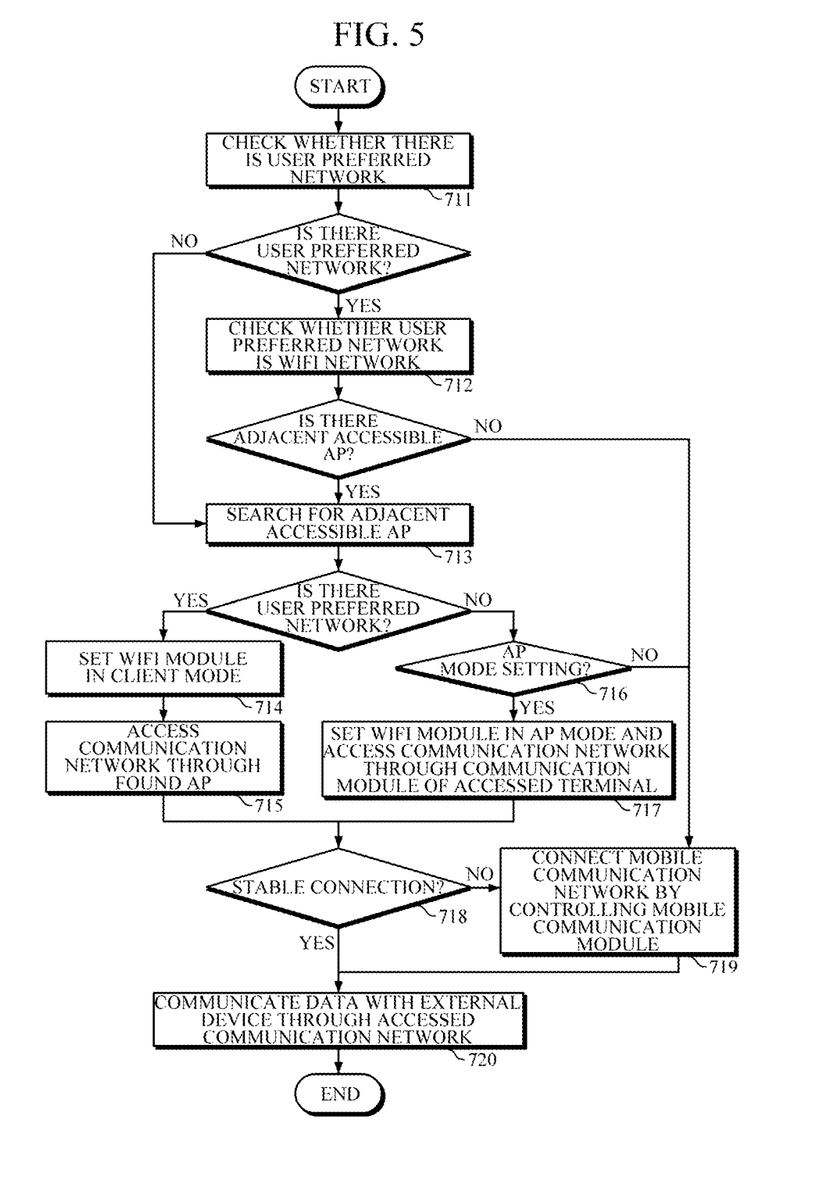
FIG. 5 is a data communication procedure in the apparatus according to yet another exemplary embodiment.

FIG. 5 is a data communication procedure in the apparatus 100 according to yet another exemplary embodiment. Referring to FIG. 5, another example in which the apparatus 100 performs data communication with the external device 200 is described.

Firstly, the apparatus 100 checks whether there is a preferred network set by a user in 711. The user may set various kinds of setting information in advance by manipulating an interface, and store the setting information in the storage 120. The user may prefer to access a WiFi network, which does not require additional costs, and set the WiFi network as the first network to be connected; however, if unlimited data usage is possible in a mobile communication network, the user may instead set, as a preferred network, the mobile communication network that enables more stable access.

If there is a user preferred network, the apparatus 100 identifies whether the user preferred network is a WiFi network in 712. If the user preferred network is a WiFi network, the apparatus 100 searches for an adjacent accessible AP 50*a* in 713. If there is no particular preferred network set by the user, the apparatus 100 first attempts to access a WiFi network, which boasts off a high communication speed and does not require additional costs, and searches for an adjacent accessible AP 50*a* in 713.

If the adjacent accessible AP 50*a* is found, the apparatus 100 may set the WiFi module in a client mode in 714 and access the WiFi network through the found AP 50*a* in 715.

In 716, the apparatus 100 may check whether the WiFi module is set to be in an AP mode in a case where no adjacent accessible AP 50*a* is found. Whether to set the WiFi module to be automatically in an AP mode may be decided by a user and information thereof may be stored in the storage 120.

If so, the WiFi module is set in the AP mode, and then the apparatus 100 waits for access of the mobile terminal 50*b* and, in response to the access of the mobile terminal 50*b*, accesses a communication network through a communication module of the mobile terminal 50*b* in 717.

Then, the apparatus 100 checks whether a connection status of the accessed communication network is stable in 718, and, if so, performs data communication with the external device 200 over the accessed communication network in 720.

Meanwhile, in a case where the user preferred network is not determined as a WiFi network in 712, where connection to a communication network is set through a mobile communication module without setting the AP mode in 716, or where a connection status of the WiFi network is not stable in 718, the apparatus 100 may control the mobile communication module 142 to connect a mobile communication network. The apparatus 100 performs data communication with the external device over an accessed communication network in 720.

Meanwhile, the embodiments of the present disclosure may be implemented by computer-readable codes in computer-readable storage media. The computer-readable storage media includes any data storage device that is capable of storing data that can be read by a computer system.

Examples of a non-transitory computer-readable storage medium include read-only memory (ROM), random-access memory (RAM), magnetic tapes, floppy disks, magneto-optical data storage devices, and carrier waves (such as data transmission through the Internet). In addition, the computer-readable storage medium can also be distributed over network coupled computer systems so that the computer readable code is stored and executed in a distributed fashion. Also, functional programs, codes, and code segments for accomplishing the present invention can be easily construed by programmers skilled in the art to which the present invention pertains.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents. Therefore, the scope of the invention is defined not by the detailed description of the invention but by the appended claims, and all differences within the scope will be construed as being included in the present invention.

The invention claimed is:

1. An apparatus for measuring biological information, comprising:
   a measuring processor configured to measure biological information using a biosensor;
   a processor configured to comprise a wireless processor comprising a WiFi processor that supports a client mode and an Access Point (AP) mode, and to transceive the measured biological information with an external device over an accessed communication network; and
   the processor configured to control the client mode or the AP mode of the WiFi processor to access a communication network,
   wherein when the processor does not find an adjacent accessible AP, the processor controls the WiFi processor to be set in AP mode;
   wherein when the WiFi processor is in AP mode, the processor waits to detect a terminal accessing the apparatus based on the AP mode setting;
   wherein the processor directly controls a communication device included in the terminal to transmit the measured biological information to the external device through the terminal.

2. The apparatus of claim 1, wherein the processor is further configured to comprise:
   the processor configured to search any adjacent accessible AP; and
   the processor configured to set the WiFi processor in the client mode in a case where an AP is found by the processor, and set the WiFi processor in the AP mode in a case where no AP is found by the processor.

3. The apparatus of claim 2, wherein the processor transmits data to the external device through the found AP in response to the WiFi processor set in the client mode.

4. The apparatus of claim 1, wherein the processor is further:
   configured to, in response to the WiFi processor set in the AP mode, control the communication device included in the terminal.

5. The apparatus of claim 1,
   wherein the measuring processor is further configured to comprise:
      a sensor connector configured to connect a biosensor; and
      a signal processor configured to convert biological signal measured by the biosensor into biological information,
   wherein the apparatus further comprises:
      a storage configured to store the converted biological information; and
      a display configured to display the converted biological information.

6. The apparatus of claim 1, wherein the wireless processor further comprises one or more of a Bluetooth device, a Zigbee device, and a Near Field Communication (NFC) device.

7. The apparatus of claim 6,
   wherein the processor is further configured to receive, from an NFC terminal connected through the NFC device, connection information of the wireless processor equipped in the NFC terminal,
   wherein the apparatus further comprises the processor configured to set connection information of a corresponding wireless processor by using the received connection information.

8. The apparatus of claim 1,
   wherein the processor is further configured to comprise a mobile communication device that comprises a third-generation (3G) or fourth-generation (4G) mobile communication device,
   wherein the processor controls any one communication device based on a communication network access status of the wireless processor and a mobile communication device, or based on information on a user preferred network so as to access a communication network.

9. A method for communicating data in an apparatus for measuring biological information, the method comprising:
controlling, by the apparatus, access to a communication network through a client mode and an Access Point (AP) mode of a WiFi device; and
transceiving data including biological information to an external device over the communication network,
wherein the controlling of access to a communication network comprises,
searching for an adjacent accessible AP and when an AP is not found, setting the WiFi device to AP mode;
when the WiFi device is in AP mode, waiting to detect a terminal accessing the apparatus based on the AP mode setting;
directly controlling a communication device included in the terminal to transmit the measured biological information to the external device through the terminal.

10. The method of claim 9, wherein the controlling of access to a communication network comprises:
searching for an adjacent accessible AP; and
setting a WiFi device in a client mode when the adjacent accessible AP is found by an AP search device, and setting the WiFi device in an AP mode in a case where the adjacent accessible AP is not found by the AP search device.

11. The method of claim 10, wherein the transceiving of data comprises, in response to the WiFi device set in the client mode, transmitting the data to an external device through the found AP.

12. The method of claim 9, wherein the wireless communication device comprises one or more of a Bluetooth device, a Zigbee device, and a Near Field Communication (NFC) device.

13. The method of claim 12, further comprising, prior to the controlling of access to the communication network,
receiving connection information of a wireless communication device equipped in an NFC terminal connected through the NFC device; and
setting connection information of a corresponding wireless communication device by using the received connection information.

* * * * *